United States Patent [19]
Plunkett

[11] Patent Number: 5,524,298
[45] Date of Patent: Jun. 11, 1996

[54] MALE GENITALS GARMENT

[76] Inventor: Robert L. Plunkett, 21141 Cañada Rd. #17D, El Toro, Calif. 92630

[21] Appl. No.: 382,782
[22] Filed: Feb. 2, 1995
[51] Int. Cl.⁶ ........................................ A41B 9/02
[52] U.S. Cl. ........................... 2/403; 602/67; 2/400
[58] Field of Search .................. 2/403, 400; 602/70–73, 602/67–69; 450/111

[56] References Cited

U.S. PATENT DOCUMENTS

| | | | |
|---|---|---|---|
| D. 233,633 | 11/1974 | Burkard | 602/67 |
| 967,736 | 8/1910 | Delp | 602/70 |
| 1,638,525 | 8/1927 | Chisholm | 602/70 |
| 3,459,181 | 8/1969 | Mann | 602/67 |
| 3,621,846 | 11/1971 | Lehman | 602/67 |
| 3,774,241 | 11/1973 | Zerkle . | |
| 4,195,630 | 4/1980 | Connery . | |
| 4,702,239 | 10/1987 | Ichikawa . | |
| 5,226,179 | 7/1993 | Choi . | |
| 5,237,706 | 8/1993 | Nalbandian . | |

Primary Examiner—C. D. Crowder
Assistant Examiner—Gloria Hale

[57] ABSTRACT

A mens' garment for surrounding and securing the genitals, having a waistband, a penis-covering front piece shaped to conform with the groin region, and a scrotal pouch that is secured to the back side of the front piece in a manner that forms at once a barrier between the penis and the scrotum and an open-ended penis-receiving sheath which secures and protects the penis, and allows for urination without removing the garment or touching the penis with the thumb and fingers. This men's garment is devoid of any between-the-legs structures used to hold the garment in place on the body or otherwise cover any portion of the buttocks. This garment's scrotal pouch employs a means of securement around the base of the scrotum and is secured to the front piece in a manner that, in conjunction with the waistband, holds the front piece in a downward position and inward toward the groin.

1 Claim, 5 Drawing Sheets

MALE GENITALS GARMENT

BACKGROUND—FIELD OF INVENTION

This invention relates to a garment for males comprised of a waistband and its attached material which surrounds and secures the genitals.

BACKGROUND—DESCRIPTION OF PRIOR ART

The market for men's genital garments has been held for decades almost solely by the traditional brief and boxer-style garments. This despite the ill-effects and complaints that have always accompanied their usage. Long-standing and various attempts to overcome the discomforts and unhealthful effects of the common snug-fitting briefs and loose-fitting boxer-style garments apparently have not been of a design that a demand for such alternative garments created even a small market. Reviewing the art of these alternative garments provokes at least several ideas as to why they have not come into widespread use, thereby suggesting that the problems solved created further problems that outweigh these initial solutions.

Most known prior art employs scrotal pouches and/or a form of separator between the scrotum and penis with various buttocks-fitting panels and/or straps to hold the garment in place: other art is of a more general loincloth design—see; U.S. Pat. No. 3,621,846 (1971) to Lehman: U.S. Pat. No. 4,195,630 (1980) to Connery; U.S. Pat. No. 4,702,239 (1987) to Ichikawa: U.S. Pat. No. 4,759,355 (1988); U.S. Pat. No. 5,226,179 (1993) to Choi: U.S. Pat. No. 5,237,706 (1993) to Nalbandian. However, it is quite apparent in such art that its actual usage, the donning and removal, requires considerable manipulation by hand of the genitals relative to that required by traditional men's briefs. While such manipulation might be considered a minor inconvenience given the purported benefits of prior art, contemporary sexual norms regarding any extensive and indiscreet handling of one's genitals are very likely to rule out the use of any design that requires little more than the traditional and simple pulling on and off of a brief-type garment and the usual and simple flipping down of a waistband in order to urinate. Known prior art makes it clear that the penis and/or scrotum must be maneuvered into, around, and/or through various openings, channels, and divides. Given the power of contemporary sexual norms, such manipulation is certain to be a cause of embarrassment in public rest rooms, gym locker-rooms, and non-private areas. Not only would this be an obvious cause of embarrassment and possible ridicule, such handling of the genitals is often quite impractical if not strongly inadvisable, given the various jobs and activities attended to by men that require them to get their hands heavily soiled and/or tainted with toxic substances—such as a mechanic, farmer, oil worker. etc. Known prior art requires various loosenings and securings of a waistband and/or the manual inserting and reinserting of the penis and/or scrotum into a pocket or pouch, operations that are neither convenient or healthful in a situation where the hands are dirty and wash facilities are unavailable. So that in addition to the cause for embarrassment noted above, known prior art requires the handling of genitals in a manner that is troublesome, impractical, and/or inadvisable. Thus, when compared to a) the now simple act of donning and removing traditional men's genital garments and b) the now simple act of urination and defecation allowed by present traditional genital garments, the more extensive handling of the genitals required by known prior art can be seen as objectionable. Prior artists have dismissed or overlooked the problem of undue genital handling as it relates to health issues and to the very strong social norms surrounding the handling of one's genitals.

Relatedly, prior art has utilized between-the-legs panels and/or strap(s) extending upward across the buttocks that can cause discomfort. The single strap of the sort found on "thong"-type briefs works deep into the cleft of the buttocks, irritating the sensitive anal skin, and soon becomes soiled, the ensuing stain and discoloration causing embarrassment in the locker room and the laundromat; dual jock-like straps cross the buttocks in a manner that imparts a distasteful and/or unprofessional straight-from-the-gym appearance, with jock-strap like lines showing through outer clothing and interrupting the natural, aesthetic curves of the buttocks. Buttocks panels of the type shown in U.S. Pat. No. 3,621,846 (1971) to Lehman, and in U.S. Pat. No. 4,702,239 (1987) to Ichikawa are of a looser diaper-type design that tends to ride upward and inward to the cleft of the buttocks when worn under outer garments, causing discomfort and providing the conditions for sweat, chaffing, and tetter. Furthermore, the free-hanging front flaps in U.S. Pat. No. 3,621,846 (1971) to Lehman, and in U.S. Pat. No. 4,195,630 (1980) to Connery allow the penis to flop freely when these garments are worn alone, thereby permitting exposure/insecurity and creating a feeling of unprotectedness; likewise, these garment flaps have a tendency to shift and ride upward under outer garments, causing exposure and/or discomfort to the penis.

Finally, such prior art is of designs and/or constructions which are visually associated with incontinence garments and/or medical problems in the genital region, thereby causing embarrassment and discouraging their use in private and public areas where men, through contemporary social acceptance, wear nothing but such a genitals-covering garment.

Therefore, the need still exists for a men's genital garment that permits the benefits of known prior art while providing for simplicity in construction, ease of use, and the absence of embarrassment—and discomfort—causing buttocks structures found in prior art. Furthermore, any such genital garment must recognize and thereby solve the problems associated with the handling of the genitals that goes beyond that prescribed by currently marketed mens' briefs, health-minded prudence, and contemporary, sexual norms. The recognition and consequent solution of these problems in the construction of a genitals-covering garment, built into a sleek and aesthetically pleasing form, will aid in that garment's reception into a market that is long overdue for some alternatives.

BRIEF SUMMARY OF INVENTION; OBJECTS AND ADVANTAGES

In its basic form the present invention includes a one-piece waistband with an attached front piece of a sculpted and tapered triangular form, this front piece extending downward to cover the groin and having a shallow cup formed in its bottom-most end. A scrotal pouch comprised of an anterior and posterior piece is attached to both sides of the rear of the front piece in a manner that forms at once a support pouch for the scrotum and an open-ended sheath to receive the penis, the anterior piece of the pouch thereby separating the penis from the scrotum. The upper posterior hem of the scrotal pouch has an elastic quality so as to hug the base of the scrotum and has a finger tab at its rear-most position to facilitate the donning of the entire garment.

Accordingly, several objects and advantages of the present invention are as follows. To provide a male genital garment:

a) that is donned as easily and with no more manipulation of the genitals than is required by presently popular briefs;

b) that employs a means of separating the scrotum from the penis that requires little or no handling of the genitals to effect such a separation;

c) that incorporates a penis receiving sheath and scrotal pouch which permit air circulation around penis and scrotum but at the same time restrict the free jostling of the penis and the testicles;

d) that eliminates the need for direct skin-to-skin contact when adjusting the penis at the time of urination;

e) that is devoid of any between-the-legs structure(s) and/or strap(s) that run up or cover any portion of the buttocks, thereby eliminating the chaffing, sweat, and itching in the rectal region caused by such structures, and furthermore, thereby allowing the passing of feces without needing to alter the wearing position of the invention in any way:

f) that is of a design which combines construction simplicity, protection against the wet spots on a covering garment after urination, and a clean, backless style that will not elicit the feelings of discomfort and visual distaste that have been associated with the diaper-look of loincloths and the jock-like straps and thin strings which interrupt the aesthetic, natural curves of the buttocks.

g) that is of a frontal design which is sleek and sexy by contemporary standards, not evoking embarrassing associations with specialized medical-related garments, and can be worn comfortably alone due to such an aesthetically pleasing look.

These and other objects and advantages will be made apparent as they reside in the details of construction and operation of the garment as it is hereinafter more fully described and claimed, reference being made to the accompanying drawings forming part hereof, wherein like reference numerals refer to like parts throughout.

BRIEF DESCRIPTION OF THE DRAWINGS

In the drawings various stitch markings have been omitted when they make unclear the basic lines of the garment and are otherwise rendered obvious in the descriptive details.

Figure 1:
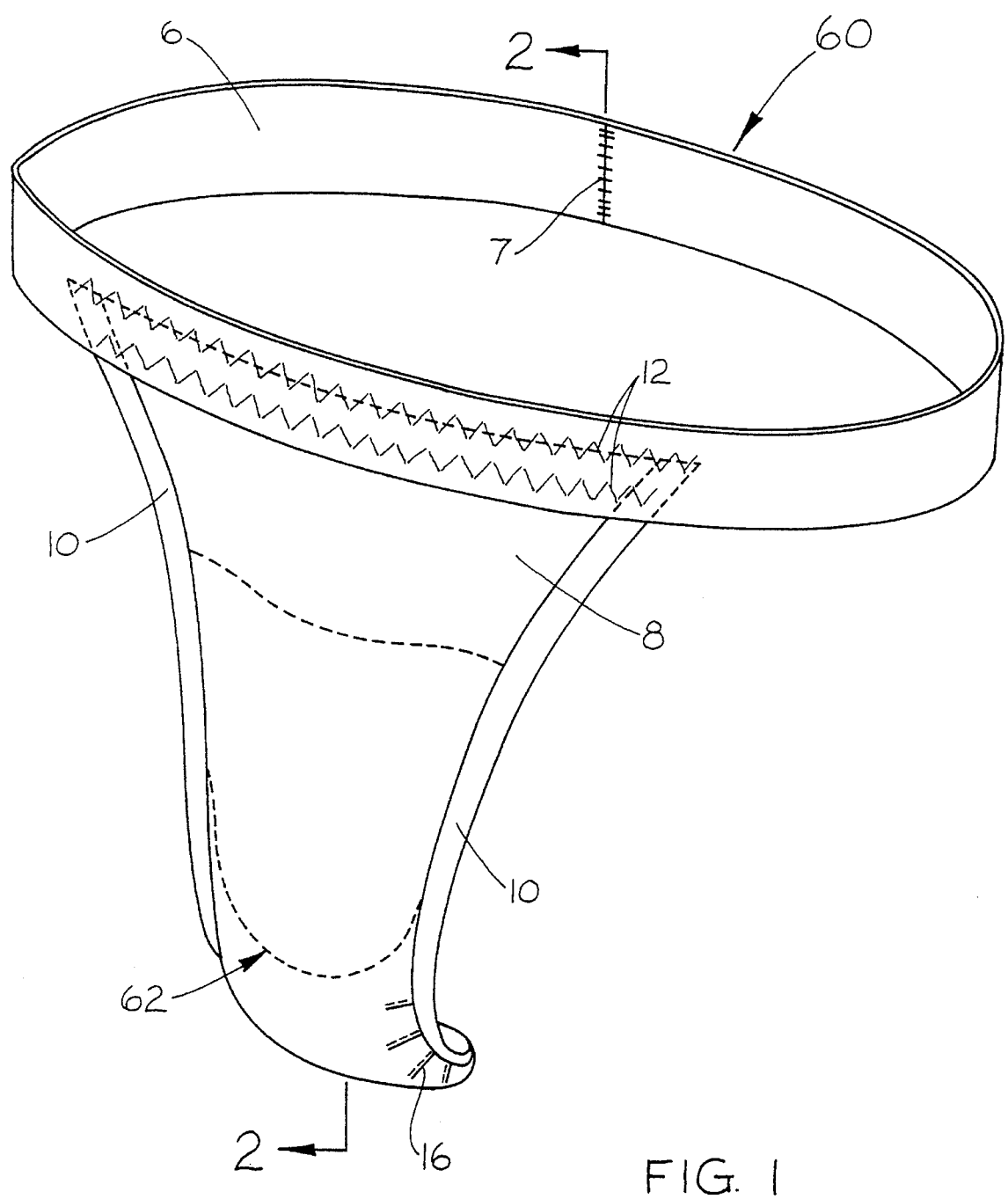
FIG. 1 is a front perspective view of the garment.

LIST OF REFERENCE NUMERALS 6 one-piece waistband
7 joining stitch
8 tapered front piece
10 edge binding
12 stretchable stitch
14 anterior scrotal pouch piece
16 stitched darts
18 posterior scrotal pouch piece
20 finger tab
22 stitched dart
23 stitched dart
24 joining stitch
26 horizontal top edge
28 substantially scalloped top edge
29 elastic band
30 sheath-forming attachment means
32 sheath-forming attachment means
34 transition point
60 male genitals garment
62 scrotal pouch

DETAILED DESCRIPTION

Figure 2:
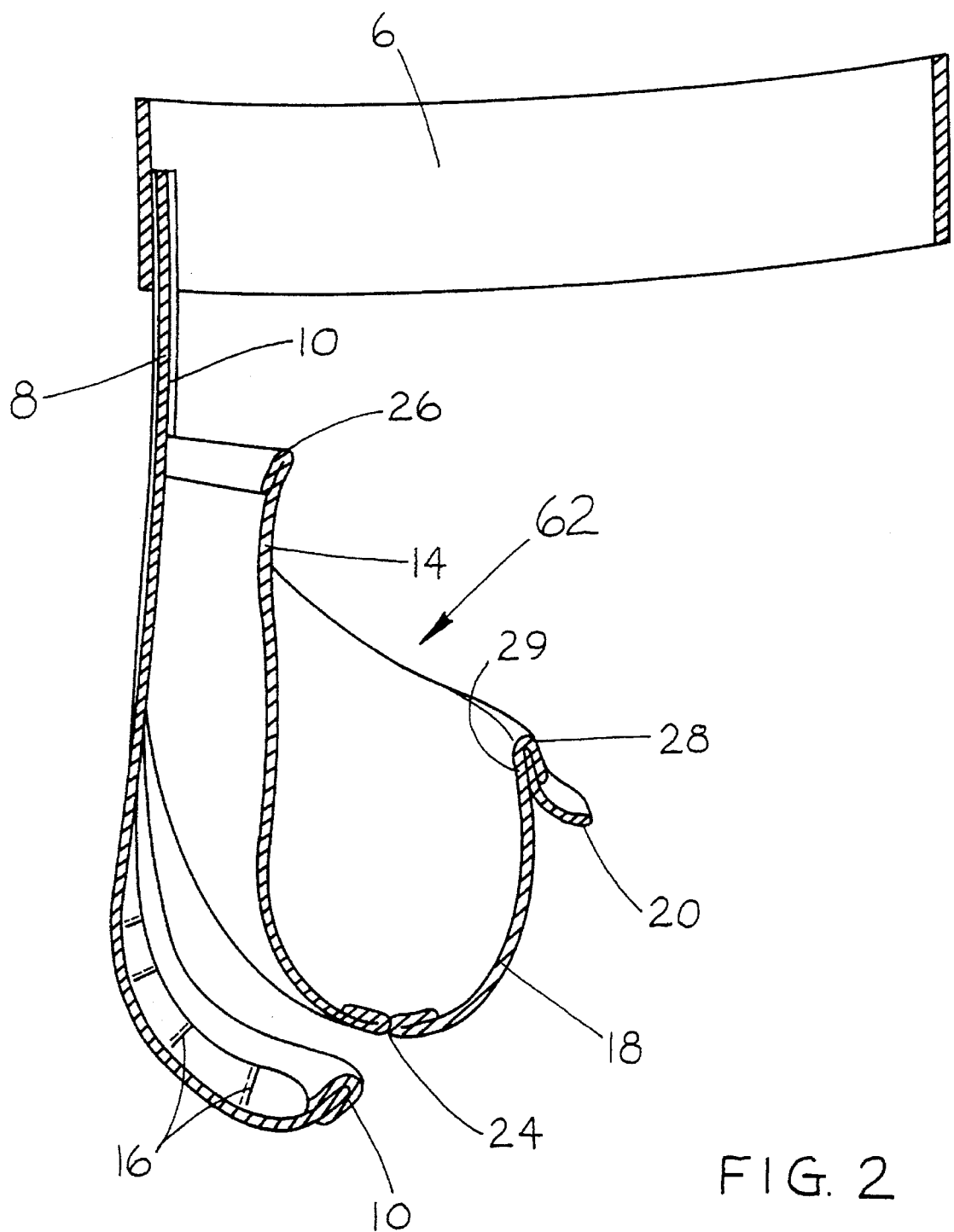
FIG. 2 is a cross section taken on line 2—2, FIG. 1.

Shown in FIG. 1 is the basic preferred embodiment of a male genitals garment 60 from a front perspective view. Garment 60 comprises a one-piece elastic waistband 6 which has its ends joined by a length of joining stitch 7. A fabric tapered front piece 8 with a preferably heavy, non-stretchable fabric edge binding 10 is attached with a double row of a stretchable stitch 12 to the rearward face of a front and central position on waistband 6 relative to joining stitch 7. Front piece 8 has a largely horizontal top edge that is of a width corresponding to the contours of the groin as they widen out to the lower abdomen where the waistband 6 is likely to be positioned on the body. Front piece 8 has inwardly arced sides that are cut to follow the contours of the male body from the lower abdomen to the groin and cut so as to be appropriate for any given male body size, front piece 8 being of a length that allows for its sides to be formed at their lower sections, by way of a series of stitched darts 16, into a somewhat blunted, rounded-edged, shallow cup that extends beyond the penis and comes up just below and midway into a scrotal pouch 62 as shown by cross-section in FIG. 2.

Figure 4:
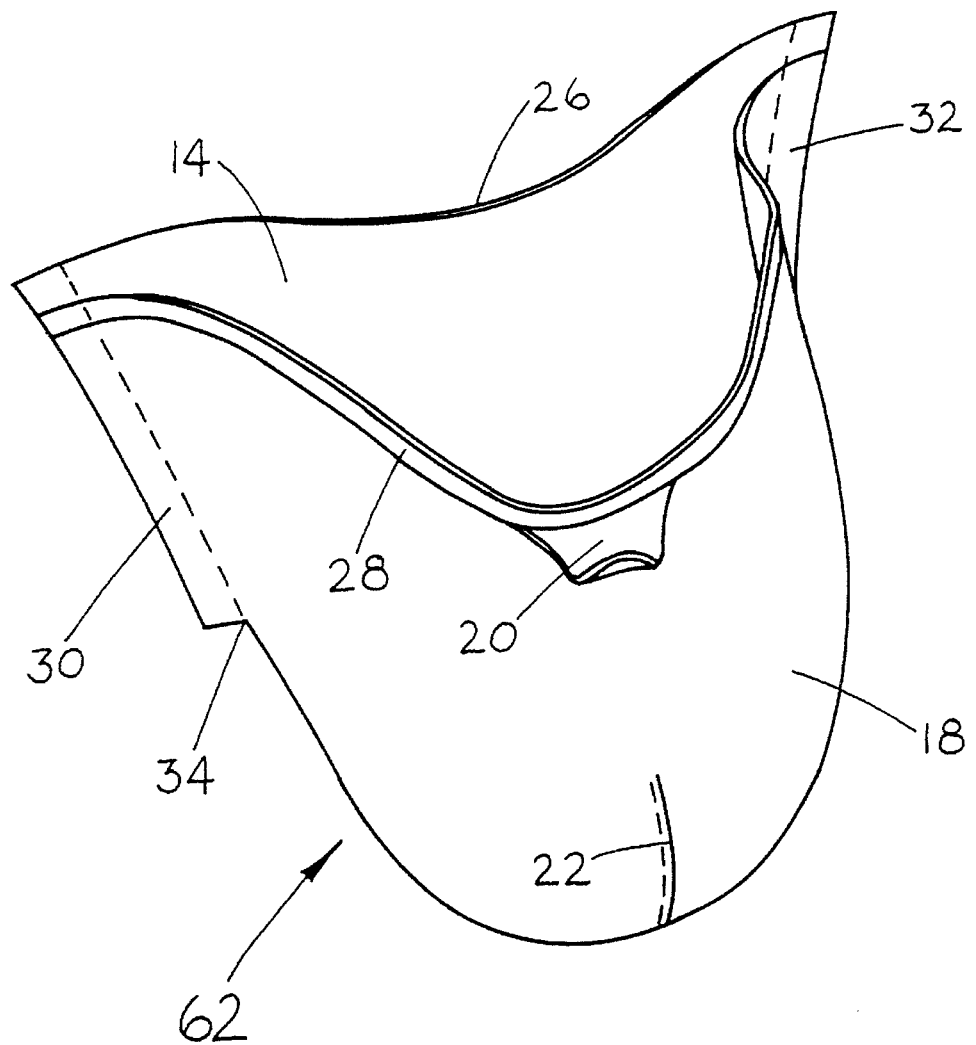
FIG. 4 is a detail perspective view of the detached scrotal pouch viewed from the rear.
Figure 5:
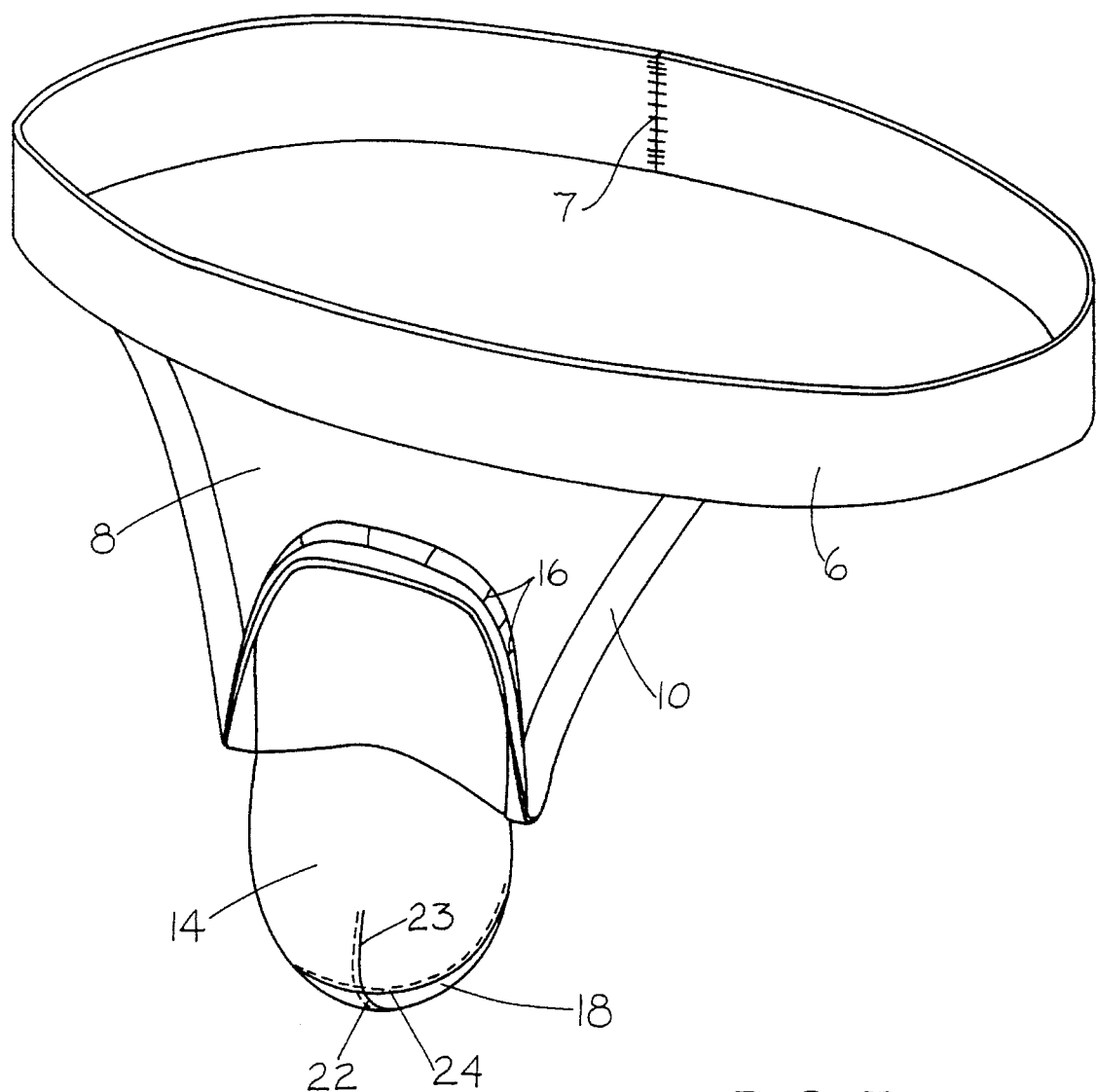
FIG. 5 is a front perspective view of the garment in a possible mode of operation which shows the front piece of the scrotal pouch.

FIG. 4 shows a scrotal pouch 62 detached from front piece 8, comprising an anterior fabric scrotal pouch piece 14, a posterior fabric scrotal pouch piece 18, and a fabric finger tab 20. Scrotal pouch piece 14, which forms the back side of the penis-receiving sheath and also forms the separating barrier between the scrotum and penis, has an outwardly hemmed, substantially horizontal top edge 26. Scrotal pouch piece 18 has an elastic band 29 (not shown) contained in an outwardly hemmed substantially scalloped top edge 28 that tapers out to horizontal ends. At a rearmost position on hemmed top edge 28 is stitched finger tab 20 such that finger tab 20 extends in a downward direction. The sides and lower sections of scrotal pouch pieces 14 and 18 are essentially of a similar shape; the overall area dimensions of these pieces can vary so as to allow the size of the pouch to be adjusted to fit a range of testicle/scrotum sizes. Cup-forming dart stitches 22 and 23, sewn into bottom sections of piece 18 and piece 14 respectively, thereby form the front half and back half of scrotal pouch 62 when then joined along their sides and lower sections with joining stitch 24, the constellation of dart stitches 22, 23 and stitch 24 being shown in FIG. 5, joining stitch 24 moving from an inwardly hemmed seam in the bottom cup portion of scrotal pouch 62, shown in FIG. 5 and by cross-section in FIG. 2, to an outwardly hemmed seam on the side portions of pieces 14 and 18, at a place shown by transition point 34 in FIG. 4, in a manner that thereby forms lengthy sheath-forming attachment means 30 and 32 on both sides of scrotal pouch 62, as still shown in FIG. 4.

Figure 3:
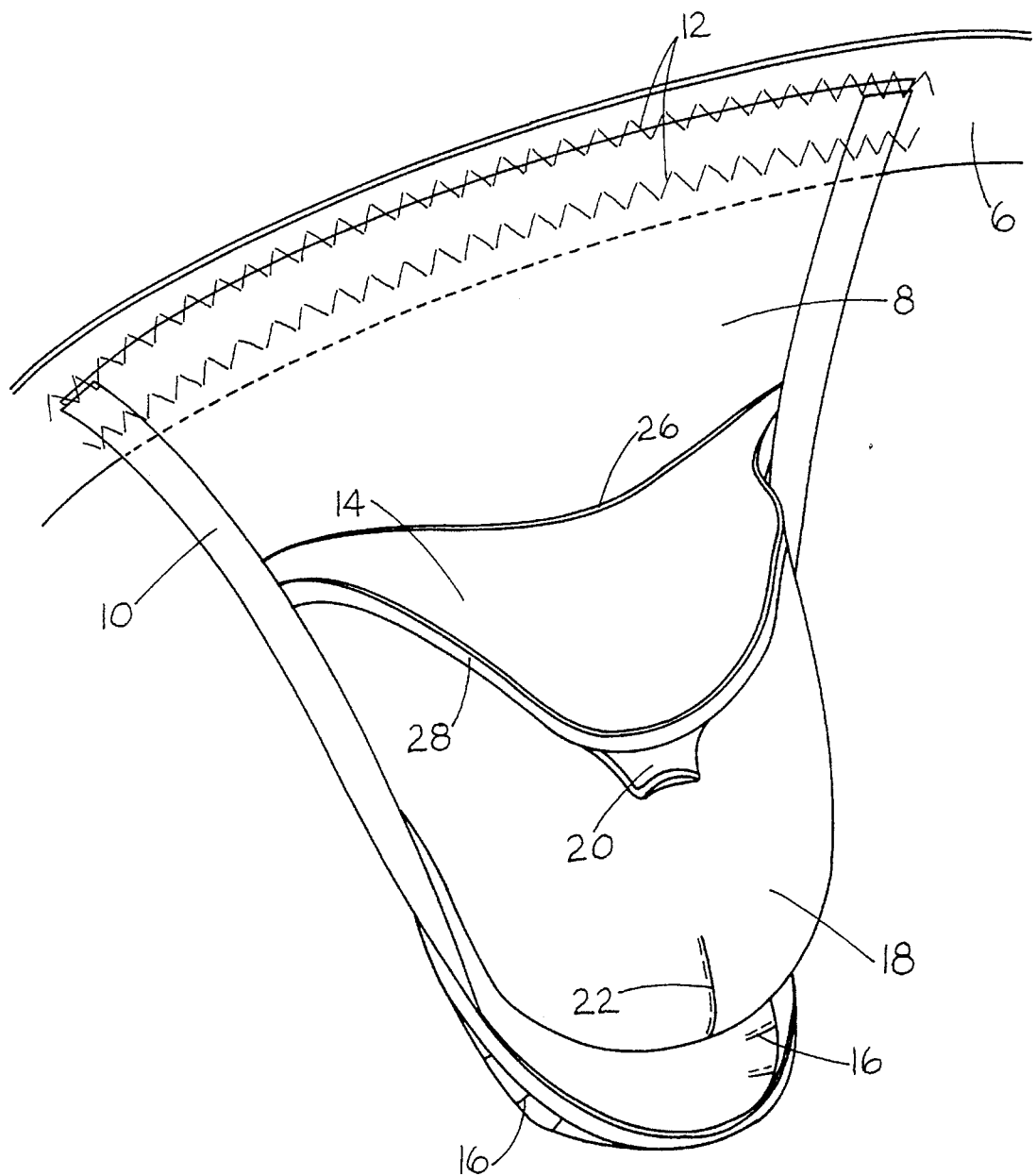
FIG. 3 is a fragmentary perspective view of the front piece of the garment viewed from the rear.

FIG. 3 shows the front fragment of garment 60 viewed from the rear with scrotal pouch 62 attached to the back side of front piece 8 by tucking scrotal pouch sheath forming attachment means 30 and 32 under edge binding 10 that runs along the sides and bottom section of front piece 8. The vertical positioning of pouch sheath forming attachment means 30 and 32 along the sides of front piece 8 is dictated by the overall size of garment 60 as it is proportioned to fit a range of male body sizes. Edge binding 10 is then stitched in place in the usual manner, the scrotal pouch being of such an overall width when attached to the back side of front piece 8 that anterior scrotal pouch piece 14 comes away from the back side of front piece 8 so that a penis receiving sheath is thereby formed. The upper horizontal edge of front piece 8, now inclusive of edge binding 10 on each end, is attached by a double row of stretchable stitch 12 to the back side of the front of one-piece waistband 6 relative to the waistband ends that are joined by stitch 7.

Operation

This garment is stepped into in the usual fashion and as it is brought up to the normal position on the waist the hanging penis guides itself into the described wide sheath opening just forward and inclusive of anterior scrotal pouch piece 14 of scrotal pouch 62, thereby eliminating the need to handle the penis. The finger tab 20 at the rear of the scrotal pouch is then grasped by the thumb and index finger to pull the pouch in a downward and rearward direction so as to capture the entire scrotum, the elastic hemmed scalloped top edge 28 of the pouch now resting snugly at the base of the scrotum where the scrotum protrudes from down under and between the legs, the pouch now fully enclosing the scrotum. The scrotal pouch being secured in this manner in turn secures the front piece 8 in towards the crotch by virtue of the attachment of the scrotal pouch to the sides of the front piece 8, thereby preventing the front piece 8 from shifting to the side or flipping up when the garment is worn alone, or from riding up when the garment is worn underneath other clothing. Let it be noted here that the inherent stiffness of the elastic hemmed scalloped top edge 28 relative to the pieces 14 and 18 of the scrotal pouch gives the pouch opening some form after a period of wear that often makes the use of the finger tab 20 unnecessary, allowing this garment to be pulled on simply by the waistband, with no manipulation of the genitals, in the same manner used in pulling on presently popular briefs and boxer shorts.

At the time of urination the sheath structure is slid up with the thumb and fingers so that the head of the penis protrudes beyond the cup-like structure at the end of front piece 8; it is then slid back down in a like manner to again cover the length of the penis. Defecation does not require any movement of the garment that is additional to that made for urination, with the side benefit of the front piece 8 now preventing the penis from accidentally touching the front inner side of a toilet seat. Of course, if this garment is pulled down around the legs in order to defecate, it can be repositioned in the above stated manner without handling the genitals. Though normally unnecessary, the design of this garment also permits it to be pulled on over the head and subsequently fitted into place again in the same manner. Such a mode of operation can be immensely useful in circumstances that do not easily allow the removal of lower body outer clothing and shoes or large boots. This over-the-head mode of operation can also be of value in emergency or physically disabling situations when the legs are in a fixed position and cannot or should not be moved.

Conclusion, Ramifications, and Scope of Invention

Through the preceding summary of advantages, descriptions, and operations of the present invention, the reader will see that this Male Genitals Garment provides an alternative to presently popular briefs and prior art, featuring designs and modes of operation that take more highly into account the anatomical structure and needs of the male body and gives full consideration to the social norms and daily life styles of the contemporary male. Furthermore, the whole of the invention is of an aesthetically pleasing design which enhances, rather than detracts from, the lines and forms of the male body and, notably, is of a construction design that permits great ease of manufacture.

While the above detailed description contains specificities, these should not be construed as limitations on the scope of the invention, but rather as an exemplification of one preferred embodiment thereof. Many other variations are possible. For example, the shallow cup at the bottom of the front piece 8 can include a fastening device that allows it to be fixed to a mating fastening device on the bottom of the scrotal pouch 62 so that the whole front piece is positively secured in a downward position. Or, the front piece 8 can be of a wrap-around design with a deeper bottom cup piece with elastic-hemmed sides so that the entire lower and bottom section of such a front piece can be pulled over the scrotal pouch and find its securing in the same manner as the scrotal pouch at the base of the scrotum. Relatedly, to the back side of the front piece 8 can be attached various barrier-faced absorbent fabrics/materials to inhibit the leaking through of urine to the outer surface of the front piece 8.

Another embodiment would substitute a from of drawstring in place of the elastic band 29 within the deeply scalloped hem 28, the drawstring then being pulled through openings in the edge binding 10 so as to make the tension of the securing hem 28 of the scrotal pouch fully adjustable. In a like manner, a further embodiment can include such a drawstring in the edge binding 10 of the front piece 8 in the above-mentioned wrap-around style, again making the tension of the securings fully adjustable. A drawstring waistband can also be part of the above embodiments, thereby keeping an integrity to the whole invention.

Lastly, the invention can be embodied in various materials for specific applications. For example, a quick-drying nylon mesh or a form-retaining nylon-backed thin neoprene rubber of the wet suit variety can be used in construction, thereby rendering the invention suitable for swim wear. Similarly, leather, or some such other material which holds a form, can be used in the construction of the invention, thereby obviating the use of various elastics and other materials employed for securing the invention around the scrotum of the user. Accordingly, the scope of the invention should be determined not by the embodiment illustrated, but by the appended claims and their legal equivalents.

I claim:

1. A male support garment comprising:

a one-piece elastic waistband;

a substantially U-shaped tapered front piece having a front side, a back side, side edges, a lower edge and a top edge;

said front piece is attached at its top edge to an inside face of said waistband;

a scrotal pouch comprised of an anterior and posterior piece;

said anterior piece of said scrotal pouch having a substantially horizontal top edge and said posterior piece having a substantially scalloped top edge tapering out to horizontal ends;

said anterior and posterior pieces each having similarly shaped side edges and bottom edges wherein the joining of said side edges of said anterior and posterior pieces forms a pouch with sheath-forming means on both side edges;

said sheath-forming means on side edges of said scrotal pouch are secured to both side edges of the back side of said front piece at a position approximately midway along the length of the front piece whereby the back side of the front piece and an anterior scrotal pouch piece form an open-ended penis receiving sheath;

said sheath being of a length that corresponds to approximately the length of the penis in a given size; and wherein said sheath-forming means on said scrotal pouch are attached to both side edges of the back side of said front piece, whereby said front piece is retained in a downward and inward position toward the wearer's groin when said scrotal pouch is fitted on the scrotum.

* * * * *